(12) United States Patent
Lee et al.

(10) Patent No.: US 6,342,359 B1
(45) Date of Patent: Jan. 29, 2002

(54) METHOD FOR DETECTING NUCLEIC ACIDS, DETECTOR FOR NUCLEIC ACIDS AND METHOD FOR PRODUCING THE SAME

(75) Inventors: Won Yong Lee, Goonpo; Je Kyun Park, Seoul; Su Hyeon Kim, Seoul; Tae Han Kim, Seoul, all of (KR)

(73) Assignee: LG Electronics Inc., Seoul (KR)

( * ) Notice: Subject to any disclaimer, the term of this patent is extended or adjusted under 35 U.S.C. 154(b) by 0 days.

(21) Appl. No.: 09/672,787

(22) Filed: Sep. 29, 2000

(30) Foreign Application Priority Data

Oct. 1, 1999 (KR) .............................................. 99-42401

(51) Int. Cl.$^7$ .............................. C12Q 1/68; C12M 1/00
(52) U.S. Cl. ........................................ 435/6; 435/285.1
(58) Field of Search ...................... 435/6, 285.1, 287.1, 435/288.5; 536/22.1, 23.1, 24.31; 252/700

(56) References Cited

U.S. PATENT DOCUMENTS 5,312,527 A * 5/1994 Mikkelson et al. ......... 435/288
5,324,457 A * 6/1994 Zhang et al. ............... 252/700

FOREIGN PATENT DOCUMENTS

WO   WO98/28444   * 7/1998

* cited by examiner

*Primary Examiner*—Eggerton A. Campbell
*Assistant Examiner*—Suryaprabha Chunduru
(74) *Attorney, Agent, or Firm*—Morgan, Lewis & Bockius LLP

(57) ABSTRACT

The present invention provides a nucleic acid detector for detecting a base sequences of a target DNA of interest, which comprises a DNA chip in which probe DNA and electrochemiluminescent material such as tris(2,2'-bipyridyl) metal complex, or derivatives thereof are immobilized on a surface of gold electrode; an electrochemical apparatus for applying a predetermined voltage to the DNA chip with respect to a reference electrode; and an optical measurement apparatus for measuring electrochemiluminescence generated from the DNA chip. The present invention also provides a method for producing the said detector for nucleic acids, and method for detecting nucleic acids using the same in a cost-saving way with high sensitivity.

20 Claims, 6 Drawing Sheets

METHOD FOR DETECTING NUCLEIC ACIDS, DETECTOR FOR NUCLEIC ACIDS AND METHOD FOR PRODUCING THE SAME

BACKGROUND OF THE INVENTION

1. Field of the Invention

The present invention relates to a method for detecting nucleic acids by electrochemiluminescence, detector for nucleic acids and method for producing the same. More particularly, the present invention is directed to a method for producing a detector for nucleic acids comprising a DNA chip which is fabricated by immobilizing electrochemiluminescent material such as $Ru(bpy)_3^{2+}$ derivatives and probe nucleic acid on a fine gold electrode by self assembly, method for selectively detecting a DNA duplex formed by complementary hybridization of DNA by electrochemiluminescence, and detector for nucleic acids.

2. Description of the Background Art

Generally, methods for detecting nucleic acids such as DNA or RNA are employed in various fields such as biological researches, medical diagnosis, new drug screening, forensic medicine, etc.

Southern blotting is one of those methods, a method for detecting DNA having a specific base sequence. That is, DNA fragments of a test sample are separated by electrophoresis, and the separated DNA fragments are moved onto a solid substrate made of nitrocellulose or nylon membrane, thereby maintaining the relative position of DNA fragments. Next, the DNA fragments fixed on the solid substrate and probe DNA labeled with a radioisotope are hybridized, by which the position of the DNA having a specific base sequence can be learned.

Northern blotting for detecting RNA was also developed by modifying the above method, and the operating principle thereof is not so different from that of the Southern blotting.

However, such a conventional nucleic acid detection method is disadvantageous in that it requires enormous labor forces, time, and resources. To overcome the above problem, DNA chip on which plurality of nucleic acids are located at a known position of the substrate in two dimensional array has been developed.

DNA chip which is formed by arranging DNA fragments of variety of base sequences on the surface of a narrow substrate in high density can be used in finding out the information on DNA of an unknown sample by hybridization between an immobilized DNA and unknown DNA sample complementary thereto. Here, the term "hybridization" means that gene subsequences are linked each other to form double-stranded DNA by complementary base pairing of hydrogen bond between the DNA bases of adenine-thymine (A—T), guanine-cytosine (G—C). Accordingly, it is possible to find out the information of DNA sequences of sample by complementarily hybridizing DNA fragments of sample of interest with DNA probes immobilized on substrate and then detecting labeled DNA probes, or DNA sample or double-stranded DNA formed by hybridization.

The most widely employed labeling method in conventional molecular biology is the radioautography in which target DNA is labeled by radioisotope. As the radioisotope, $^{32}P$ or $^{35}S$ or the like is generally used, and the binding state of labeled target DNA and the probe DNA can be detected using photographic films. This method can be easily utilized since it does not require much basic knowledge. However, it is disadvantageous in that, the result cannot be obtained immediately because the detection time takes several hours or even a day, the resolution is in the order of no more than 0.1 through 10 $\mu$m. Further, the radioisotope used as a label does not ensure human's safety.

Therefore, laser-induced fluorescence is widely used recent days. This method has advantages that various luminescent materials are available, and the resolution is fine. In addition, in case of applying a CCD camera to the above method, molecules labeled by luminescent material can be imaged as soon as they are linked with one another, thereby enabling a rapid determination of the result. However, it is disadvantageous in that this method, though most widely used, requires a process for covalently bonding these molecules with luminescent material before measuring DNA sample of interest, and expensive equipments such as a laser, optical measuring attachment, etc. Moreover, as disclosed in U.S. Pat. No. 5,091,652, it also requires a high-priced image scanner in order to scan the two-dimensional surface of the substrate.

Another method used as a nucleic acid detection method is the optical detection method (P. A. Stimpson et al., *Pro. Natl. Sci. USA*, 91(1995) 6379–6383). The above method is to make evanescent waves using a two-dimensional optical wave guide and light scattering, and to make the waves scattered at a label adsorbed to a DNA capture region on the surface of the wave guide. Particles functioning as the above label are concentrated only at the portion where probe oligomer and DNA fragments are linked, which causes light scattering. In this optical detection method, it is very convenient because the cleaning step is not required. The detection step does not need much time because the hybridization pattern of chips can be directly checked with eyes by a CCD camera or 8mm video camera. However, this method also requires expensive equipments.

In addition, researches on the method for detecting a DNA binding without using a label by surface plasmon resonance (SRP) are recently underway. This method is advantageous in that since changes in refractive index and thickness occurring in the interface between the metallic surface of a thin layer and a solution are detected, DNA binding can be easily detected without using a label. However, the above method has a disadvantage that detection is possible only when approximately $10^{11}$ probe DNA is immobilized on the surface of 1 $cm^2$ due to its poor sensitivity.

U.S. Pat. No. 5,312,527 relates to a method for electrochemical detection of DNA hybridization, wherein the results of DNA hybridization is detected using the binding between an electrochemically active metal complex and a double-stranded DNA. Though the manufacturing cost can be reduced, it is disadvantageous in that it has a poor sensitivity.

As described above, the conventional nucleic acid detection methods all have various disadvantages, and thus there has been a need to develop a new method in order to solve these problems. In particular, it is required to develop a method for rapidly detecting a hybridization with DNA with a fine sensitivity without performing a process of covalently bonding a sample with a tracer in advance, and moreover, a small, low-priced detection system for development of a portable diagnostic apparatus.

SUMMARY OF THE INVENTION

Accordingly, the present invention provides a low-priced detector for nucleic acids with a high sensitivity by electrochemiluminescence, method for producing the same, diagnostic kit for detecting nucleic acids, and method for detecting nucleic acids.

BRIEF DESCRIPTION OF THE DRAWINGS

The present invention will become better understood with reference to the accompanying drawings which are given only by way of illustration and thus are not limitative of the present invention, wherein.

DETAILED DESCRIPTION OF THE PREFERRED EMBODIMENTS

Figure 1:
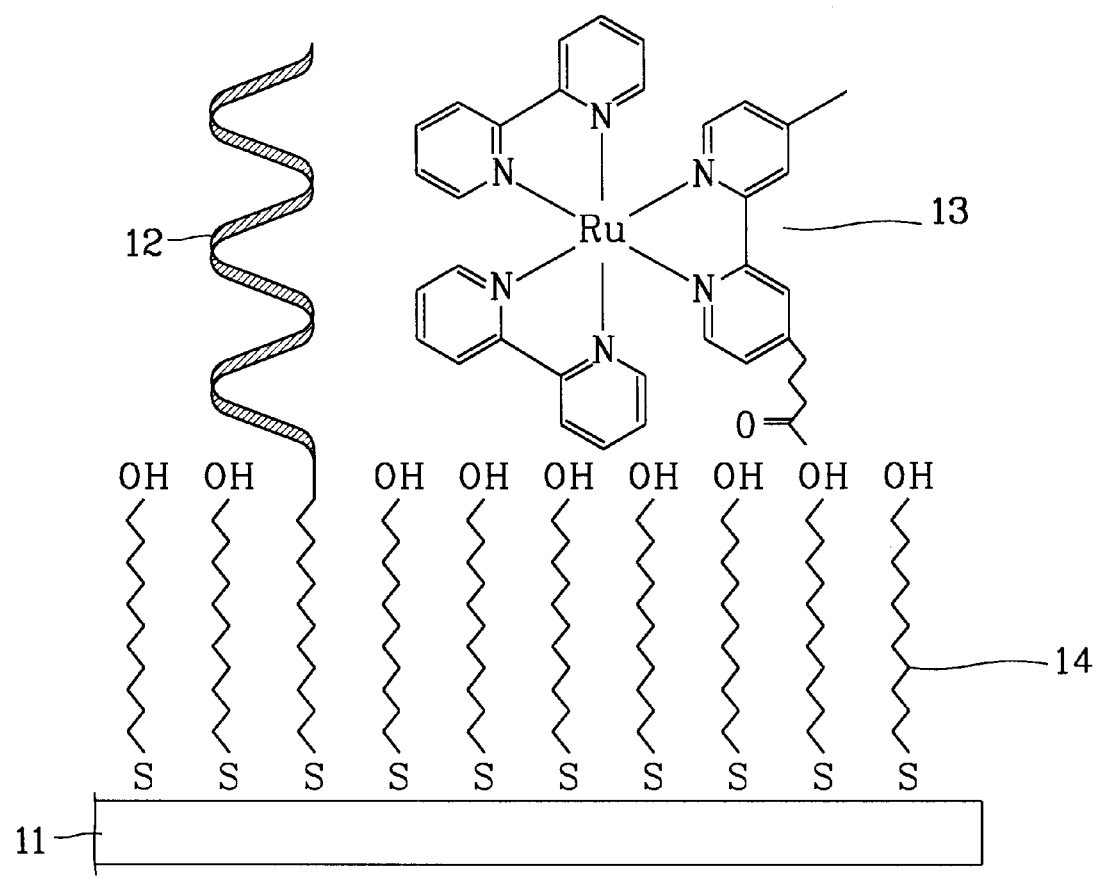
FIG. 1 is a view illustrating the structure of a DNA chip according to the present invention.

The present invention relates to a detector for nucleic acids, method for producing the same, and method for detecting nucleic acids. More particularly, the present invention relates to a method for selectively detecting hybridization between probe nucleic acids immobilized on a chip or sensor of respective DNA chip or DNA sensor and target nucleic acids present in a physiological sample by using electrochemiluminescence emitted by a transition metal complex, and detector for nucleic acids.

The present invention provides a nucleic acid detector for detecting a base sequence of a target DNA, which comprises: a DNA chip in which probe DNA and electrochemiluminescent material such as tris(2,2'-bipyridyl) metal complex, or derivatives thereof are immobilized on a surface of gold electrode; an electrochemical apparatus for applying a predetermined voltage to the DNA chip with respect to a reference electrode; and an optical measurement apparatus for measuring electrochemiluminescence generated from the DNA chip.

The above electrochemiluminescent material according to the present invention is preferably $Ru(bpy)_3^{2+}$ or $Os(bpy)_3^{2+}$.

The above probe DNA may be a single stranded DNA which complementarily hybridize with the target DNA.

The electrochemical apparatus may be a three-electrode system or two-electrode system.

In case of selecting the three-electrode system, the DNA chip serves as a working electrode, an Ag/AgCl electrode or silver wire can be used as a reference electrode, a platinum wire can be used as a counter electrode. A potentiostat (62) can be further used in order to adjust the applied voltage between the reference electrode and the working electrode. Alternatively, in case of selecting the two-electrode system, the DNA chip serves as the working electrode, and the ground or the platinum wire can be used as the counter electrode. At this time, a battery can replace the potentiostat in applying a voltage.

The optical measurement apparatus for measuring electrochemiluminescence preferably comprises an optical detector(66), optical counter(67), A/D converter(68), and computer(69).

On the one hand, as the above optical detector for detecting chemiluminescence, an APD(avalanche photodiode), PMT(photomultiplier tube), or the like can be used, or a cooled CCD camera or peltier-type CCD camera can be used in order to detect various positions. Since the detector for nucleic acids according to the present invention does not detect target nucleic acids by labeling a tracer, a light source such as an additional laser or LED and filter used in fluorometry are not necessary. In addition, because the aforementioned luminescence is a light generated by electrochemical reaction, a light source for filtering luminescent material is not necessary, either. Accordingly, the detector for nucleic acids according to the present invention has advantages that detection with a high sensitivity is realizable because noise and scattering due to the light source can be minimized, and the manufacturing unit price of the overall detector for nucleic acids is lowered because the optical measurement apparatus for measuring chemiluminescence is very simple. In addition, it is possible to manufacture a portable scanner by using an APD (avalanche photodiode) as the optical measurement apparatus and using a battery in applying a voltage.

In addition, the present invention provides another detector for nucleic acids which is characterized in that the said DNA chip is an electrode in which a plurality of different probe DNAs are respectively immobilized at a plurality of different positions of the gold surface along with tris(2,2'-bipyridyl) metal complex, or derivatives thereof.

On the other hand, the target DNA in the physiological sample can be amplified in advance by polymerase chain reaction (PCR) and the like.

The target DNAs in the physiological sample are hybridized with the probe DNAs on the DNA chip to thus form a DNA duplex, and thereafter a solution containing an intercalating agent is applied to the DNA duplex to be intercalated into the same. The non-intercalated agents are removed. Then it becomes possible to monitor the intercalated agent by electrochemiluminescence which in turn enables to monitor the DNA duplex.

As an intercalating agent which selectively intercalates into the DNA duplex, all sorts of intercalating agents frequently used in conventional electrochemical detection methods are possible. Preferably, a compound having an alkyl amine group is preferred.

Meanwhile, in the case of using derivatives of $Ru(bpy)_3^{2+}$ as an electrochemiluminescent material, about 1.2V of oxidation voltage is applied to the electrodes on the DNA chip, and in case of using the derivatives of $Os(bpy)_3^{2+}$ as the electrochemiluminescent material, about 0.6V of oxidation voltage is applied. At this time, redox reaction occurs between the oxidized derivatives of $Ru(bpy)_3^{3+}$ or $Os(bpy)_3^{3+}$ and intercalating agent having alkyl amine group which is located near the electrodes, thereby forming derivatives of $Ru(bpy)_3^{2+*}$ or $Os(bpy)_3^{2+*}$ of excited state. When these excited derivatives return to the ground state, light of about 610 nm is generated. At this time, the metal complex returns to the initial oxidation state of +2, which turns to oxidation state of +3 by the applied oxidation voltage and reacts again with the intercalating agent to thus generate light. That is, during applying of a voltage, the transition metal complex generates electrochemiluminescence until all the intercalating agents are consumed.

In addition, the detector for nucleic acids and method for detecting nucleic acids according to the present invention is applicable to the method for detecting a material such as glucose by immobilizing enzyme instead of probe nucleic acids on gold electrode along with a Ru(bpy)$_3^{2+}$ derivative complex by self-assembly for thereby inducing chemiluminescence. For example, the detector for nucleic acids of the present invention can be utilized as a multibiosensor for simultaneously analyzing and detecting substances such as glucose, by using chemiluminescence caused by the reaction of Ru(bpy)$_3^{2+}$ complex and NADH which is formed upon the oxidization of materials such as glucose, lactate, ethanol, and etc. with dehydrogenase. The above detector for nucleic acids also can be used as an immunosensor when it is applied to the immunoassay by immobilizing antibody and Ru(bpy)$_3^{2+}$ in the same way, and labeling the antigen contained in the physiological sample with glucose and the like.

It is another object of the present invention to provide a diagnostic kit for detecting a base sequence of a target DNA which comprises: a physiological sample containing target DNA; a DNA chip wherein probe DNA capable of complementarily hybridizing with the said target DNA and tris(2, 2'-bipyridyl) metal complex or derivatives thereof are immobilized on a surface of gold electrode; an intercalating agent which can be intercalated into DNA duplex formed by complementary hybridization of the above target DNA and probe DNA; electrochemical apparatus for applying a predetermined voltage to the DNA chip with respect to a reference electrode; and an optical measurement apparatus for measuring electrochemiluminescence generated by redox reaction between the said tris(2,2'-bipyridyl) metal complex or derivative thereof and the intercalating agent.

It is another object of the present invention to provide a method for fabricating a DNA chip for use in a detector for nucleic acids in order to analyze a base sequence of a target DNA which includes the steps of: (1) depositing thin gold film on a substrate to form an electrode; (2) washing the electrode of the step (1); (3) soaking the above electrode of step (2) in a mixed solution in which self-assembly materials, such as probe DNAs, tris(2,2'-bipyridyl) metal complex or derivatives thereof, and (ω-hydroxy undecanethiol or 3-mercaptopropionic acid are dissolved in a certain solvent, whereby the above three self-assembly materials are self-assembled on the electrode; and (4) washing the electrode after the step (3).

At this time, the substrate can be made of borosilicate glass or silicon wafer.

The method for fabricating DNA chip can further comprises the step of forming a plurality of thin films between the substrate and the gold electrode.

The washing step (2) is preferably carried out by sequentially washing the substrate with piranha solution and then water.

It is preferred that the certain solvent of the step (3) is a mixed solvent of ethanol/octane.

Preferably, the above self-assembly materials are probe DNA, tris(2,2'-bipyridyl) metal complex or derivatives thereof, and ω-hydroxyundecanethiol. In the aspect of electron transfer reaction between electrode and metal complex, it is preferred that the self-assembly reaction time of the step (3) is adjusted in such a manner that the three self-assembly materials cover about 50% of the electrode surface.

The mixed solution of step (3) is preferably a solution made by dissolving Ru(bpy)$_3^{2+}$ or Os(bpy)$_3^{2+}$ transition metal complex or derivatives thereof, which is synthesized by introducing an alkylthiol functional group at one pyridyl ligand, probe DNA having an alkylthiol functional group at the phosphate group of 5'-end, and ω-hydroxyundecanethiol in a mixed solvent of ethanol/octane. It is more preferred that the ratio of the metal complex, probe DNA, and ω-hydroxyundecanethiol is about 1:1:8.

The washing step (4) is a process of sequentially washing the substrate with ethanol and water.

On the other hand, the present invention provides a nucleic acid detection method for detecting a base sequence of a target DNA which comprises the steps of: 1) preparing physiological sample containing target DNA in the detector for nucleic acids according to the present invention in order to form DNA duplex by complementary hybridization of probe DNA and target DNA; 2) binding the DNA duplex with an intercalating agent; 3) oxidizing tris(2,2'-bipyridyl) metal complex or derivatives thereof by applying a voltage to the electrode of the detector for nucleic acids; 4) exciting the oxidized tris(2,2'-bipyridyl) metal complex or derivatives thereof by the redox reaction with the intercalating agent; and 5) measuring the amount of light emitted when the oxidized tris(2,2'-bipyridyl) metal complex or derivatives thereof returns to the ground state.

Additional advantages, objects and features of the invention will become more apparent from the description which follows.

EXAMPLES

Method for Producing a Detector for Nucleic Acids

FIG. 1 is a view illustrating the structure of a DNA chip according to the present invention.

Firstly, probe DNA (12) and electrochemiluminescent material (13) such as derivatives of tris(2,2'-bipyridyl) ruthenium(II) (Ru(bpy)$_3^{2+}$) or tris(2,2'-bipyridyl) osmium (II) (Os(bpy)$_3^{2+}$) (13) are immobilized on the surface of a gold electrode (11) which was formed on substrate by self assembly to form a monolayer, which will now be described in order.

As the substrate, silicon wafer or borosilicate glass substrate(51) can be used. First, silicon dioxide (SiO$_2$) (52) is deposited on the substrate at a thickness of about 1000 Å by plasma enhanced chemical vapor deposition. Next, chrome (Cr) is vapor-deposited in vacuum at a thickness of about 800 Å, and then gold of 1000 Å thickness is vapor-deposited in vacuum. After coating positive photoresist on the deposited substrate, light is irradiated thereon through a mask having a predetermined pattern, and then the photo-decomposed photoresist is removed by development. Next, after etching exposed gold portions (53), silicon nitride (Si$_3$N$_4$) (54) is deposited thereon at a thickness from 3000 Å to 5000 Å using the PECVD.

Next, a washing process is required to immobilize DNA and transition metal complex on the surface of the gold electrode by self-assembly. As a washing liquid, a piranha solution made by heating the mixed solution of strong sulfuric acid and 30% H$_2$O$_2$ in the ratio of 3:1 at 100° C. is used. The electrode is soaked for a few seconds in the piranha solution, and thereafter is finally washed with water.

Afterwards, the electrode is soaked for ten minutes in a mixed solution in which derivatives of a Ru(bpy)$_3^{2+}$ or Os(bpy)$_3^{2+}$ transition metal complex, which are synthesized by introducing an alkylthiol functional group at one pyridyl ligand, probe DNA having thiol functional group at the position of 5'-end phosphate, and ω-hydroxyundecanethiol are dissolved in the mole ratio of 1:1:8 in a mixed solvent of ethanol/octane. Then, the electrode is sequentially washed with ethanol and water, and thereby the fabrication of the DNA chip is finished. The ω-hydroxy undecanethiol (14) used at this time serves to prevent the adsorption of a non-specific DNA onto the surface of the electrode. However, in the case that the surface of the electrode is covered with the above-mentioned self-assembly material at 100%, the electron transfer reaction between the electrode and the transition metal complex is made difficult. Thus, it is preferred to adjust the time of self-assembly reaction so as for the surface of the electrode to be covered about 50% level. Alternatively, 3-mercaptopropionic acid containing hydrocarbon of small length can be used in place of ω-hydroxyundecanethiol. In this case, the electron transfer can be easily done irrespective of surface coverage.

Figure 5:
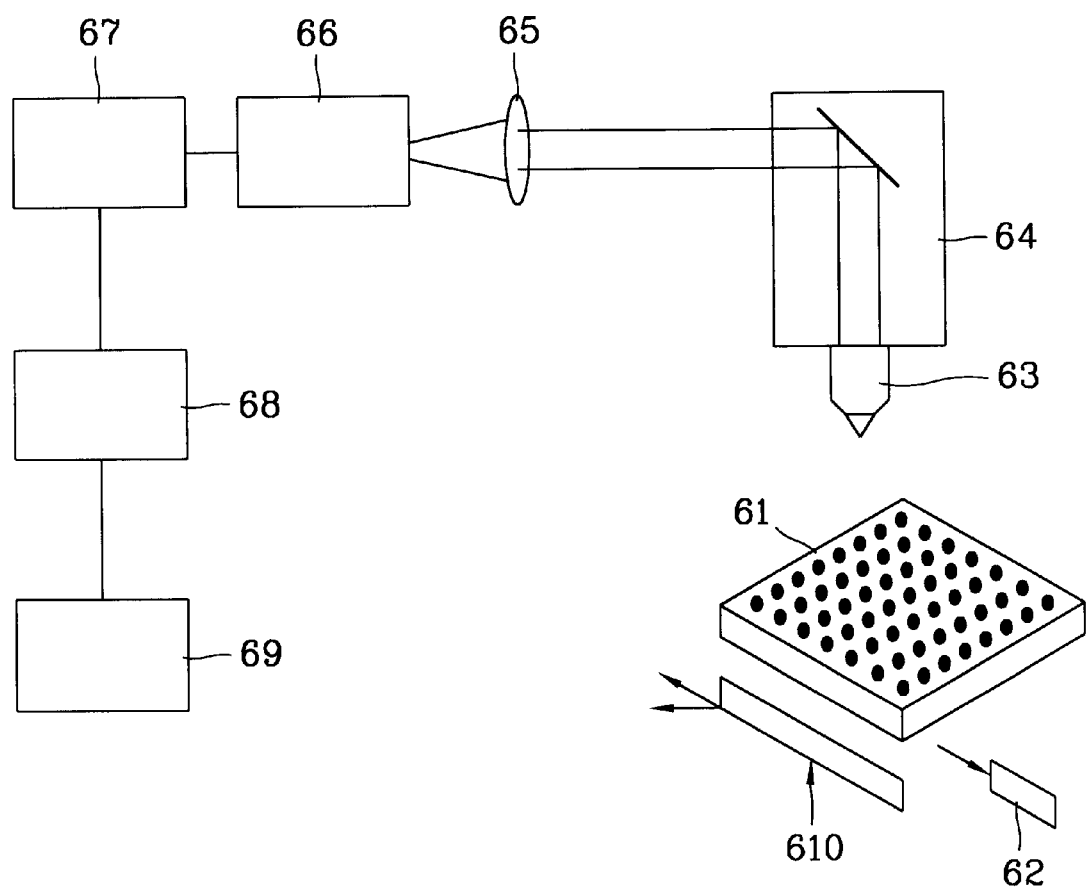
FIG. 5 is a view schematically illustrating the overall structure of the detector for nucleic acids according to the present invention.

The electrode used in the embodiment is constructed as a three-electrode system, which comprises the DNA chip acting as a working electrode, a reference electrode and a counter electrode. The above reference electrode and counter electrode are not contained in the DNA chip, but they act as extra electrodes. In other words, as shown in FIG. 5, the reference electrode and the counter electrode can be attached side by side next to the objective lens unit (63) for measuring chemiluminescence. At this time, Ag/AgCl (3M NaCl) or a silver wire can be used as a quasi reference electrode, and platinum is used as the counter electrode.

In case of immobilizing a small number of DNAs on the DNA chip, the reference electrode and the counter electrode can be fabricated together at a position adjacent to the working electrode on which the DNAs and transition metal complex are immobilized. At this time, the counter electrode is fabricated as a platinum electrode at a thickness of about 1000 Å by vapor deposition, and the reference electrode is fabricated by vapor depositing silver at a thickness of about 1000 Å.

Meanwhile, a DNA chip for detecting various target DNAs also can be fabricated.

Figure 3:
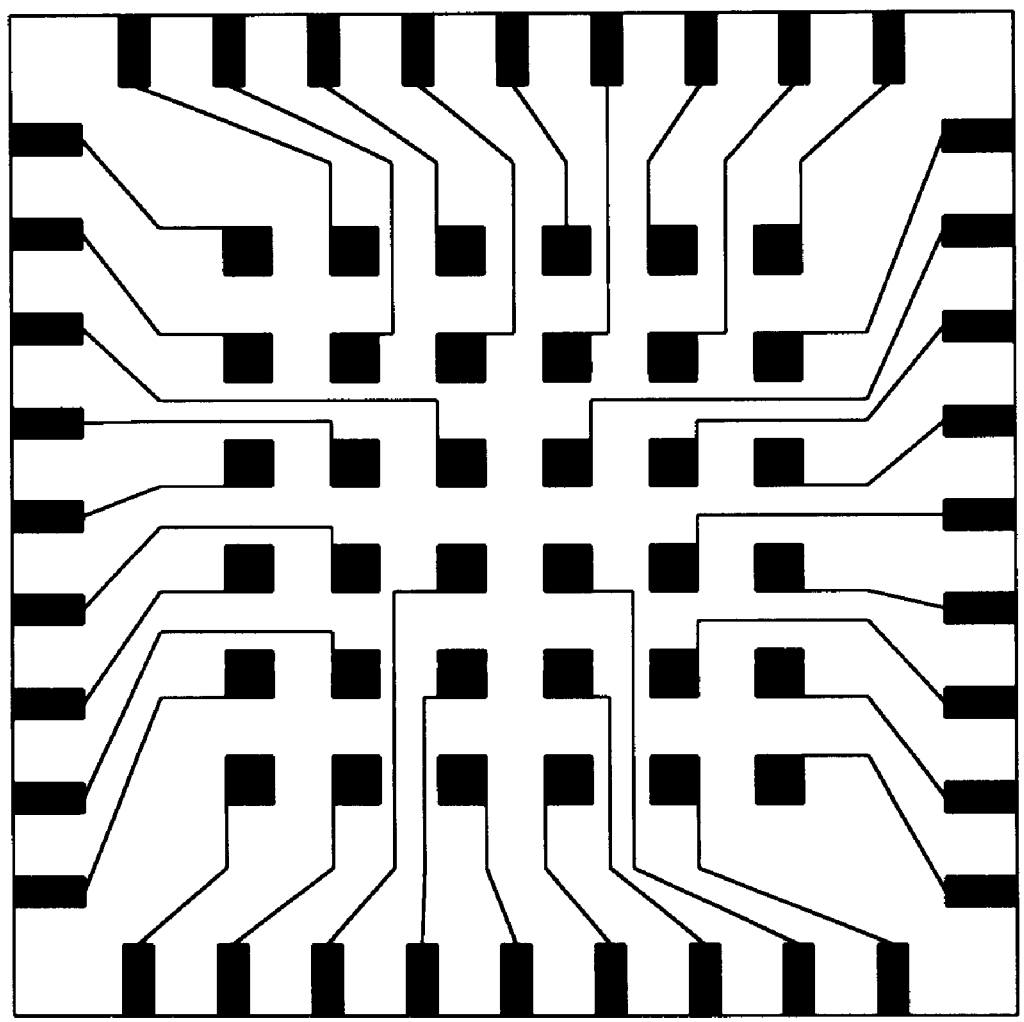
FIG. 3 is a plane view of a DNA chip in which many different probe DNAs are immobilized at respective positions of the surface of a gold electrode according to the present invention.

FIG. 3 is a plane view of a DNA chip in which many different probe DNAs are respectively immobilized at 36 positions. By means of these probe DNAs, many different target DNAs can be detected. To explain this more specifically, a cross-sectional view of parts of the DNA chip is illustrated in FIG. 4.

Figure 4:
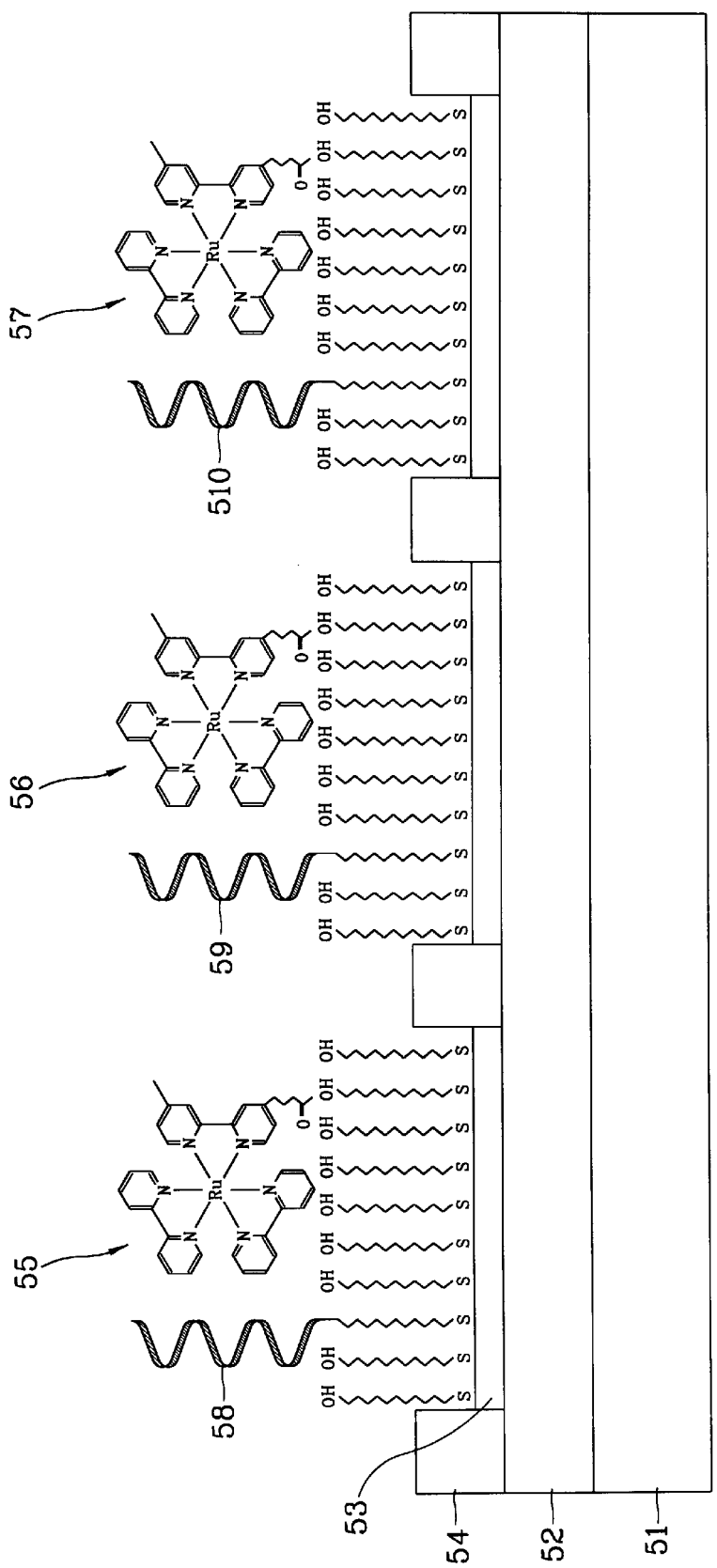
FIG. 4 is a cross-sectional view of a part of the DNA chip as illustrated in FIG. 3.

As illustrated in FIG. 4, different probe DNAs (58), (59), and (510) are immobilized at positions (55), (56), and (57) along with derivatives of $Ru(bpy)_3^{2+}$. It is possible to fabricate the DNA chip by a general semiconductor process, such as the use of a relatively simple mask, optical etching technique, etc.

At the respective position (55), (56), and (57) of the fabricated DNA chip, a mixed solution containing different probe DNAs, $Ru(bpy)_3^{2+}$ complex, and ω-hydroxy undecanethiol in the mole ratio of 1:1:8 is immobilized by the micro spotting method. In this way, different target DNAs corresponding to these different probe DNAs can be immobilized at their corresponding positions by immobilizing the respective probe DNA at its respective position.

Method for Detecting Nucleic Acids

Figure 2A:
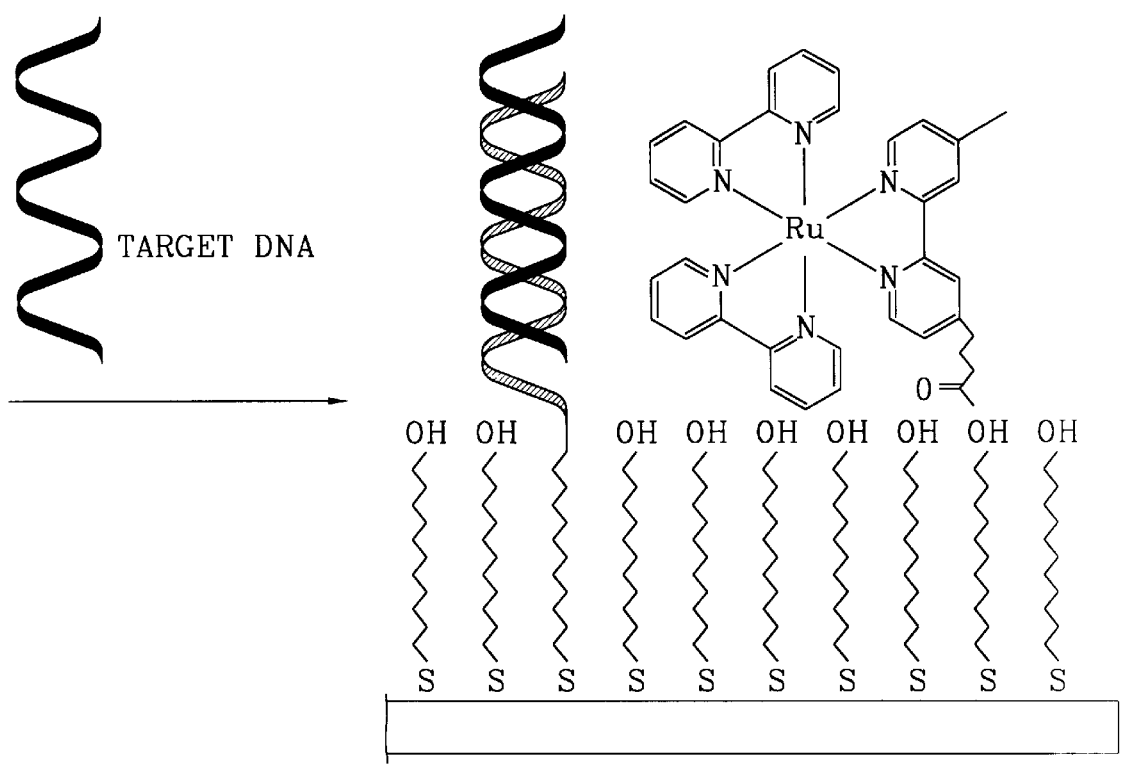
FIG. 2A is a schematic view of a process of forming a DNA duplex by hybridization when a target DNA is given to a DNA chip containing probe DNA according to the present invention.

FIG. 2A is a schematic view of a process for forming a DNA duplex by hybridization when target DNA is given to a DNA chip containing the fabricated probe DNA.

The above DNA hybridization is carried out under the conditions of a general binding reaction. At this time, if an anode voltage is applied to the electrode, a negatively charged target DNA rapidly moves to the electrode, for thereby making the hybridization with a complementary probe DNA easier. After the hybridization of DNA, a cathode voltage is applied to the electrode to remove non-complementary DNAs remaining unhybridized with the probe DNA.

Figure 2B:
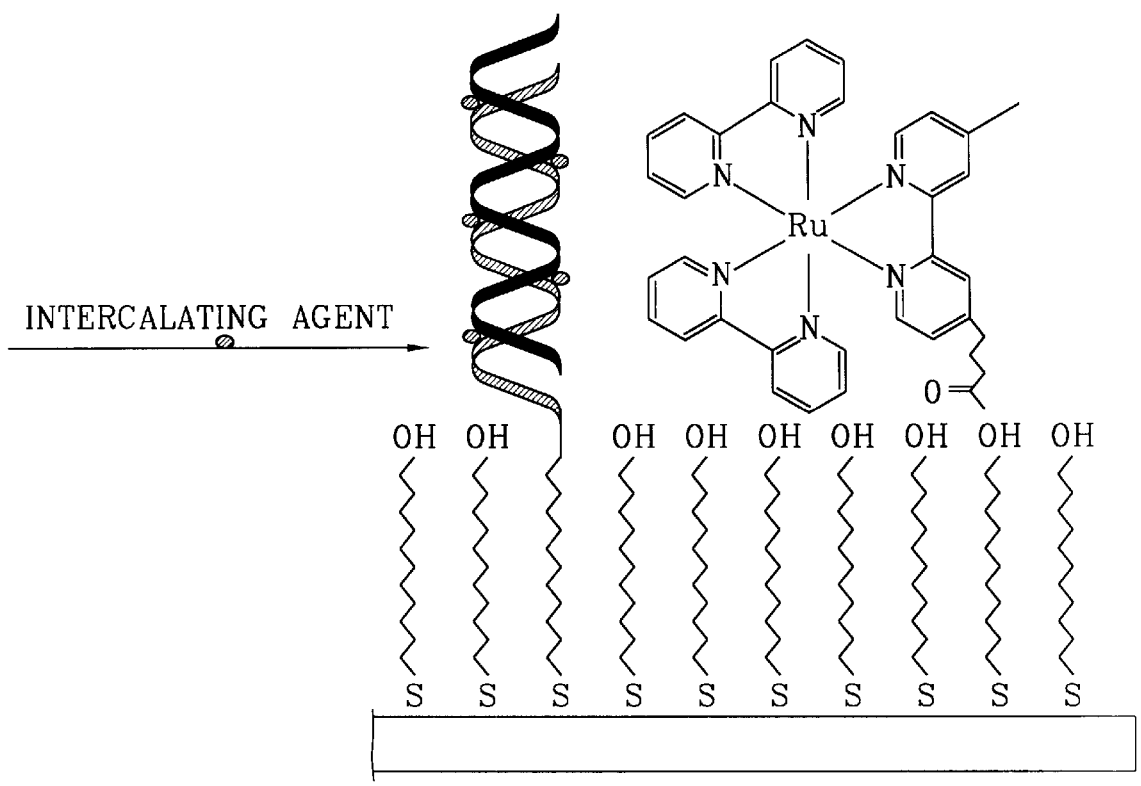
FIG. 2B is a schematic view illustrating the intercalation of an intercalating agent into a minor groove of DNA duplex in the detector for nucleic acids according to the present invention.

FIG. 2B is a schematic view illustrating a process of intercalating an intercalating agent into a minor groove of the DNA duplex by applying the intercalating agent to the DNA chip after hybridization. The intercalation reaction is applicable to the electrochemical measuring method (K. Hashimoto, K. Ito, Y. Ishimori, *Anal. Chem.*, 66(1994) 3830–3833).

Generally, it is known that $Ru(bpy)_3^{2+}$ or $Os(bpy)_3^{2+}$ emit light of strong intensity when they are reacted with the compounds having alkyl amine group. (W. Y. Lee and T. A. Nieman, *Anal. Chem.* 67(1995) 1789–1796). The electrode bound with the intercalating is subject to washing to remove the non-intercalated intercalating agent. At this time, the amount of intercalating agent intercalated into the DNA duplex is proportional to the amount of DNA duplex on electrode, which in turn is proportional to the amount of target DNA present in a physiological sample.

In case of using derivatives of $Ru(bpy)_3^{2+}$ as an electro-chemiluminescent material at the electrode on the DNA chip, a voltage of about +1.2V is applied to the electrode, and in case of using derivatives of $Os(bpy)_3^{2+}$, a voltage of about +0.6V is applied to the electrode. The derivatives of $Ru(bpy)_3^{3+}$ or $Os(bpy)_3^{3+}$ oxidized by the above process forms excited to derivatives of $Ru(bpy)_3^{2+*}$ or $Os(bpy)_3^{2+*}$ by redox reaction with the intercalating agent having an alkylamine group positioned near the electrode. These derivatives generate an orange-colored light of about 610 nm when they return to the ground state. By the above luminescence, the metal complex returns to the initial oxidized state of the positive bivalent (+2) state, and thereafter returns to the oxidized state of the positive trivalent (+3) state by an oxidization voltage applied to the electrode, thereby generating light by reaction with the intercalating agent. In other words, during the application of the voltage, the transition metal complex generates chemiluminescence until all the intercalating agent positioned at the electrode are consumed up. The above-described process will now be expressed by the following chain reaction formula.

(1) $Ru(bpy)_3^{2+}$ - - - $^{+1.2V}\rightarrow Ru(bpy)_3^{3+}$
(2) intercalating agent+$Ru(bpy)_3^{3+}\rightarrow Ru(bpy)_3^{2+*}$+oxide of intercalating agent
(3) $Ru(bpy)_3^{2+*}\rightarrow Ru(bpy)_3^{2+}$+light (about 610 nm)

The amount of light generated at this time is proportional to the amount of intercalating agent, and the amount of intercalating agent is proportional to the amount of target DNAs contained in the physiological sample. Thus, The measured amount of light is in direct proportion to the amount of target DNAs contained in the physiological sample The probe DNAs of the fabricated DNA chip are hybridized with the target DNAs, and thereafter a solution containing an intercalating agent is applied so that the intercalating agent is intercalated into the hybridized DNA duplex, and the non-intercalated agent are removed, whereby it is made possible to monitor the intercalated intercalating agent by electrochemiluminescence, which in turn enables to monitor the hybridized DNA duplex.

A chip reader can be used for the above optical measurement. When a voltage of about 1.2V with respect to a reference electrode is applied to the electrode at a position among a number of positions of the DNA chip, the $Ru(bpy)_3^{2+}$ immobilized at the electrode is oxidized into $Ru(bpy)_3^{3+}$. By redox reaction between the oxidized Ru(bpy)$_3^{3+}$ complex and the intercalating agent, a light of about 610 nm is generated, the said light is incident on a head portion of the chip reader. The head portion consists of optical parts such as an objective lens(63), mirror (64), etc. The chemiluminescence incident on the head multiplies light in a PMT or APD(avalanche photodiode) via the lens (65), and is changed into an electrical signal by an optical sensor having a high sensitivity.

On one hand, when it is desired to measure the results of the DNA hybridization at other positions, a X-Y translator (610) having the DNA chip(61) thereon is moved, and at the same time a new voltage is applied, for thereby moving the DNA chip to other positions. By repeating this process, the results of the hybridization occurred at all positions on the DNA chip can be sequentially detected.

On the other hand, when a cooled CCD camera using liquid nitrogen or a peltier-type CCD camera is used, and the same oxidization voltage is applied to the electrode at all positions on the DNA chip, the results of the DNA hybridization at all positions on the DNA chip can be simultaneously detected, for thereby enabling a rapid detection.

As the present invention may be embodied in several forms without departing from the spirit or essential characteristics thereof, it should also be understood that the above-described embodiments are not limited by any of the details of the foregoing description, unless otherwise specified, but rather should be constructed broadly within its spirit and scope as defined in the appended claims, and therefore all changes and modifications that fall within the meets and bounds of the claims, or equivalences of such meets and bounds are therefore intended to be embraced by the appended claims.

According to the detector for nucleic acids and method for detecting nucleic acids of the present invention, the results of selective hybridization between immobilized probe nucleic acids and target nucleic acids can be detected with a high sensitivity, and no complicated labeling process for covalently binding the tracer with the physiological sample is required, thereby enabling a simple, rapid detection.

In addition, the hybridization reaction of nucleic acids can be improved by adjusting the voltage of the electrode of the detector for nucleic acids according to the present invention.

The method for detecting nucleic acids of the present invention is a method for measuring electrochemiluminescence, wherein no external light source is required, and thus no light source, such as a laser, or filter is required, so that a low-priced measurement system is possible, and at the same time noise and scattering due to the light source is minimized, thereby enabling a high-sensitive analysis and detection.

What is claimed is:

1. A nucleic acid detector for detecting a base sequence of a target DNA, which comprises:
    a DNA chip in which probe DNA and electrochemiluminescent material tris(2,2'-bipyridyl) metal complex, or derivatives thereof are immobilized on a surface of gold electrode;
    an electrochemical apparatus for applying a predetermined voltage to the DNA chip with respect to a reference electrode; and
    an optical measurement apparatus for measuring electrochemiluminescence generated from the DNA chip.

2. The detector of claim 1, wherein the probe DNA is a single stranded DNA which can complementarily hybridize with the target DNA.

3. The detector of claim 1, wherein the electrochemiluminescent material is preferably Ru(bpy)$_3^{2+}$ or Os(bpy)$_3^{2+}$.

4. The detector of claim 1, wherein the electrochemical apparatus is of a three-electrode system or of a two-electrode system.

5. The detector of claim 1, wherein the DNA chip is an electrode on which a plurality of different probe DNAs are immobilized at a plurality of different positions of the gold surface along with tris(2,2'-bipyridyl) metal complex, or derivatives thereof.

6. The detector of claim 4, wherein the electrochemical apparatus is of a three-electrode system consisting of a DNA chip as a working electrode, a platinum wire as a counter electrode, and an Ag/AgCl electrode or silver wire as a reference electrode.

7. The detector of claim 1, wherein the optical measurement apparatus comprises an optical detector, optical counter, A/D converter, and computer.

8. A method for fabricating a DNA chip of the detector of claim 1, comprising the steps of:
    (1) depositing thin gold film on a substrate to form an electrode;
    (2) washing the electrode of the step (1);
    (3) soaking the above electrode of step (2) in a mixed solution in which self-assembly materials such as probe DNAs, tris(2,2'-bipyridyl) metal complex or derivatives thereof, and ω-hydroxyundecanethiol or 3-mercaptopropionic acid are dissolved in a solvent, whereby the above three self-assembly materials are self-assembled on the electrode; and
    (4) washing the electrode after the step (3).

9. The method of claim 8, which further comprises the step of forming a plurality of thin films between the substrate and the gold.

10. The method of claim 8, wherein the self-assembly materials are probe DNAs, tris(2,2'-bipyridyl) metal complex or derivatives thereof, and ω-hydroxyundecanethiol, whereupon the self-assembly reaction time of the step (3) is adjusted such that the three self-assembly materials cover about 50% of the electrode surface.

11. The method of claim 8, wherein the mixed solution is a solution dissolved with tris(2,2'-bipyridyl) transition metal complex or derivatives thereof synthesized by introducing alkyl thiol functional group on one pyridyl ligand, probe DNAs having an alkylthiol functional group 5'-end phosphate portion, and ω-hydroxyundecanethiol in a mixed solvent of ethanol/octane.

12. The method of claim 11, wherein the mixed solution contains tris(2,2'-bipyridyl) metal complex, probe DNA, and ω-hydroxyundecanethiol in the mole ratio of 1:1:8.

13. A nucleic acid detection method for detecting a base sequence of a target DNA by using the detector according to claim 1 which comprises the steps of:
    (1) preparing physiological sample containing target DNA in the detector according to claim 1 in order to form DNA duplex by complementary hybridization of probe DNA and target DNA;
    (2) binding the DNA duplex with an intercalating agent;
    (3) oxidizing tris(2,2'-bipyridyl) metal complex or derivatives thereof by applying a voltage to the electrode of the detector for nucleic acids;
    (4) exciting the oxidized tris(2,2'-bipyridyl) metal complex or derivatives thereof by the redox reaction with the intercalating agent; and
    (5) measuring the amount of light emitted when the oxidized tris(2,2'-bipyridyl) metal complex or derivatives thereof returns to the ground state.

14. The method of claim 13, wherein the target DNA in the physiological sample is amplified in advance by polymerase chain reaction(PCR).

15. The method of claim 13, wherein $Ru(bpy)_3^{2+}$ or $Os(bpy)_3^{2+}$ is used as the tris(2,2'-bipyridyl) metal complex, or derivatives thereof.

16. The method of claim 13, wherein the intercalating agent is a compound having an alkyl amine group.

17. A diagnostic kit for detecting a base sequence of a target DNA, comprising:

a physiological sample containing target DNA;

a DNA chip wherein probe DNA capable of complementarily hybridizing with the said target DNA and tris(2,2'-bipyridyl) metal complex or derivatives thereof are immobilized on a surface of gold electrode;

an intercalating agent which can be intercalated into DNA duplex formed by complementary hybridization of the above target DNA and probe DNA;

electrochemical apparatus for applying a predetermined voltage to the DNA chip with respect to a reference electrode;

and an optical measurement apparatus for measuring electrochemiluminescence generated by redox reaction between the said tris(2,2'-bipyridyl) metal complex or derivative thereof and the intercalating agent.

18. The diagnostic kit of claim 17, wherein the tris(2,2'-bipyridyl) metal complex or derivatives thereof is $Ru(bpy)_3^{2+}$ or $Os(bpy)_3^{2+}$.

19. The diagnostic kit of claim 17, wherein the intercalating agent is a compound having a alkyl amine group.

20. The diagnostic kit of claim 17, wherein the DNA chip of the diagnostic kit is fabricated by the steps of:

(1) depositing thin gold film on a substrate to form an electrode;

(2) washing the electrode of the step (1);

(3) soaking the above electrode of step (2) in a mixed solution in which self-assembly materials such as probe DNAs, tris(2,2'-bipyridyl) metal complex or derivatives thereof, and ω-hydroxyundecanethiol or 3-mercaptopropionic acid are dissolved in a solvent, whereby the above three self-assembly materials are self-assembled on the electrode; and (4) washing the electrode after the step (3).

* * * * *